(12) United States Patent
Abraham et al.

(10) Patent No.: US 8,698,641 B2
(45) Date of Patent: Apr. 15, 2014

(54) BODY FLUID DISCRIMINATING SENSOR

(75) Inventors: Jose K Abraham, Neenah, WI (US);
Davis-Dang Nhan, Appleton, WI (US);
Thomas M. Ales, III, Neenah, WI (US);
Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 265 days.

(21) Appl. No.: 13/207,603

(22) Filed: Aug. 11, 2011

(65) Prior Publication Data
US 2012/0109087 A1    May 3, 2012

Related U.S. Application Data

(60) Provisional application No. 61/409,314, filed on Nov. 2, 2010.

(51) Int. Cl.
*G08B 21/00* (2006.01)

(52) U.S. Cl.
USPC ............... 340/604; 340/568.1; 340/539.1

(58) Field of Classification Search
USPC ........ 340/604, 603, 605, 573.5, 568.1, 572.1, 340/573.1, 539.11, 539.1
See application file for complete search history.

(56) References Cited

U.S. PATENT DOCUMENTS

| | | | |
|---|---|---|---|
| 4,068,221 A | 1/1978 | McClilntock | |
| 4,100,324 A | 7/1978 | Anderson et al. | |
| 4,191,950 A | 3/1980 | Levin et al. | |
| 4,571,750 A | 2/1986 | Barry | |
| 4,704,116 A | 11/1987 | Enloe | |
| 4,768,023 A | 8/1988 | Xie | |
| 4,926,871 A | 5/1990 | Ganguly et al. | |
| 4,940,464 A | 7/1990 | Van Gompel et al. | |
| 5,284,703 A | 2/1994 | Everhart et al. | |
| 5,322,067 A | 6/1994 | Prater et al. | |
| 5,350,624 A | 9/1994 | Georger et al. | |
| 5,454,376 A | 10/1995 | Stephens et al. | |
| 5,486,166 A | 1/1996 | Bishop et al. | |
| 5,490,846 A | 2/1996 | Ellis et al. | |
| 5,709,222 A | 1/1998 | Dravallous | |
| 5,766,389 A | 6/1998 | Brandon et al. | |
| 5,820,973 A | 10/1998 | Dodge, II et al. | |
| 5,845,644 A | 12/1998 | Hughes et al. | |

(Continued)

FOREIGN PATENT DOCUMENTS

| | | |
|---|---|---|
| EP | 0 997 125 A1 | 3/2000 |
| EP | 1 092 151 B1 | 8/2008 |

(Continued)

OTHER PUBLICATIONS

Written Opinion and Search Report for PCT/IB2011/054222 dated Apr. 20, 2012.

*Primary Examiner* — Daniel Previl
(74) *Attorney, Agent, or Firm* — Dority & Manning, P.A.

(57) ABSTRACT

The present subject matter relates to absorbent articles and signaling devices for use therewith. The signaling device can be configured to detect the presence of an insult in the absorbent article and/or in an undergarment. The signaling device can be further configured to determine whether the insult is a urine insult or a feces insult. The signaling device can provide a notification to a user that an insult has occurred and can inform the user whether the insult is a urine insult or a feces insult.

20 Claims, 12 Drawing Sheets

(56) References Cited

U.S. PATENT DOCUMENTS

| | | | |
|---|---|---|---|
| 6,110,111 A | 8/2000 | Barnard | |
| 6,163,262 A | 12/2000 | Wu | |
| 6,200,250 B1 | 3/2001 | Janszen | |
| 6,221,460 B1 * | 4/2001 | Weber et al. | 428/131 |
| 6,342,037 B1 | 1/2002 | Roe et al. | |
| 6,359,190 B1 | 3/2002 | Ter-Ovanesyan et al. | |
| 6,399,853 B1 | 6/2002 | Roe et al. | |
| 6,484,053 B2 | 11/2002 | Leelamanit et al. | |
| 6,580,013 B1 | 6/2003 | Belloso | |
| 6,613,028 B1 * | 9/2003 | Daley et al. | 604/385.01 |
| 6,645,190 B1 | 11/2003 | Olsen et al. | |
| 6,677,859 B1 | 1/2004 | Benson | |
| 6,727,404 B2 * | 4/2004 | Ruman et al. | 604/378 |
| 6,731,215 B2 | 5/2004 | Harms et al. | |
| 6,774,800 B2 | 8/2004 | Friedman et al. | |
| 6,929,819 B2 | 8/2005 | Underhill et al. | |
| 7,176,344 B2 | 2/2007 | Gustafson et al. | |
| 7,221,279 B2 | 5/2007 | Nielsen | |
| 7,394,391 B2 | 7/2008 | Long | |
| 7,477,156 B2 | 1/2009 | Long et al. | |
| 7,498,478 B2 * | 3/2009 | Long et al. | 604/361 |
| 7,649,125 B2 | 1/2010 | Ales, III et al. | |
| 7,833,177 B2 | 11/2010 | Long | |
| 2003/0028165 A1 | 2/2003 | Curro et al. | |
| 2004/0220538 A1 | 11/2004 | Panopoulos | |
| 2005/0156744 A1 | 7/2005 | Pires | |
| 2005/0195085 A1 | 9/2005 | Cretu-Petra | |
| 2005/0251036 A1 | 11/2005 | Abuhamad | |
| 2006/0008972 A1 | 1/2006 | Ales et al. | |
| 2006/0244614 A1 | 11/2006 | Long | |
| 2007/0024457 A1 | 2/2007 | Long | |
| 2007/0048709 A1 | 3/2007 | Ales, III | |
| 2007/0142797 A1 | 6/2007 | Long et al. | |
| 2007/0142799 A1 * | 6/2007 | Ales et al. | 604/361 |
| 2008/0048786 A1 | 2/2008 | Feldkamp et al. | |
| 2008/0054408 A1 | 3/2008 | Tippey et al. | |
| 2008/0077040 A1 | 3/2008 | Ales et al. | |
| 2008/0077042 A1 | 3/2008 | Feldkamp et al. | |
| 2008/0132859 A1 | 6/2008 | Pires | |
| 2008/0243099 A1 | 10/2008 | Tippey et al. | |
| 2008/0266122 A1 | 10/2008 | Ales et al. | |
| 2009/0005748 A1 | 1/2009 | Ales et al. | |
| 2009/0062756 A1 | 3/2009 | Long et al. | |
| 2009/0124990 A1 * | 5/2009 | Feldkamp et al. | 604/361 |
| 2009/0157025 A1 | 6/2009 | Song et al. | |
| 2009/0326417 A1 | 12/2009 | Ales et al. | |
| 2009/0326493 A1 | 12/2009 | Wada et al. | |
| 2010/0114047 A1 | 5/2010 | Song et al. | |
| 2010/0164733 A1 | 7/2010 | Ales et al. | |
| 2010/0168702 A1 | 7/2010 | Ales, III et al. | |
| 2010/0219841 A1 | 9/2010 | Feldkamp et al. | |
| 2010/0222696 A1 | 9/2010 | Feldkamp et al. | |

FOREIGN PATENT DOCUMENTS

| | | |
|---|---|---|
| WO | WO 00 25836 | 5/2000 |
| WO | WO 00/37009 | 6/2000 |
| WO | WO 02/47592 | 6/2002 |
| WO | WO 2006/016147 | 2/2006 |
| WO | WO 2007/027219 A1 | 3/2007 |
| WO | WO 2009/063358 | 5/2009 |

* cited by examiner

BODY FLUID DISCRIMINATING SENSOR

RELATED APPLICATIONS

The present application claims priority to U.S. Ser. No. 61/409,314, filed on Nov. 2, 2010, which is incorporated herein by reference in its entirety.

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

Irritant diaper dermatitis (IDD) occurs when body waste such as feces and urine is in prolonged contact with skin. IDD is more susceptible in babies due to the sensitive nature of their skin. Frequent and prolonged skin contact with stool due to fecal incontinence and diarrhea are high risk factors for severe IDD. Many of these risks can be overcome by recent innovations in absorbent article technology, including absorbent articles having superabsorbent layers, reduced skin wetness, and superior pH control. The prevention of feces in contact with skin for a prolonged period, however, still poses a challenge. For instance, many absorbent articles include hydrophobic liquid permeable inner layers that permit urine to pass through the layer so that the urine does not contact the skin even after multiple insults. However, since feces cannot be completely absorbed into the layers of the absorbent article, prolonged contact with the skin is inevitable.

Various types of moisture or wetness indicators have been suggested for use with absorbent articles. These wetness indicators, however, fail to discriminate between body fluids such as urine and feces. For instance, known wetness indicators often cannot discriminate between feces, sweat, and urine. This could mislead a user and adds an additional burden to an already overloaded caregiver.

Many known wetness indicators are based on electrical detection using conductive elements separated by a distance on any of the layers of the absorbent article. These wetness indicators detect a change in an electrical property, such as impedance, due to the presence of an ionic liquid such as urine. The change in the electrical property triggers an alarm to indicate the presence of wetness in the absorbent article. Fecal indicators are also implemented using gas sensors such as hydrogen sulfide sensors, ammonia sensors and other biological compound sensors. But these are not capable of urine detection. Since most of these wetness indicators are highly sensitive to urine, none of them can clearly discriminate between a urine insult and a fecal insult.

Thus, a body fluid discriminating sensor that can discriminate between body exudates such as urine and feces is highly desired. A sensor that informs the caregiver that the absorbent article has been spoiled and of the particular type of insult would be particularly useful.

SUMMARY

Aspects and advantages of the invention will be set forth in part in the following description, or may be obvious from the description, or may be learned through practice of the invention.

One exemplary embodiment of the present disclosure is directed to a signaling device for detecting and identifying an insult in an absorbent article. The signaling device includes a sensor configured to provide an output signal associated with an electrical property of the absorbent article. The electrical property changes in response to an insult. The signaling device further includes an electronic circuit coupled to the sensor. The electronic circuit is configured to analyze the output signal to determine whether the insult is a urine insult or a feces insult.

In a variation of this exemplary embodiment, the sensor can be an impedance sensor adapted to monitor changes in impedance due to an insult. For instance, in a particular embodiment, the impedance sensor can be configured to monitor the impedance between a first conductive element and a second conductive element disposed in the absorbent article. The first conductive element and the second conductive element can be positioned in the absorbent article such that the impedance between the first conductive element and the second conductive element varies in response to an insult. The first conductive element and the second conductive element can be separated from an absorbent structure in the absorbent article by a barrier layer. The output signal of the impedance sensor is based at least in part on the impedance between the first conductive element and the second conductive element.

In a particular aspect of this exemplary embodiment, the electronic circuit can be configured to classify the insult as a urine insult if the output signal returns to within a threshold of its original value within a defined time period after a change in the output signal due to the insult. In another particular aspect of this exemplary embodiment, the electronic circuit can be configured to classify the insult as a feces insult if the output signal remains substantially constant for a defined time period after a change in the output signal due to the insult.

In another variation of this exemplary embodiment, the impedance sensor includes an induction coil sensor located external to the absorbent article. The output signal is based at least in part on the impedance of the induction coil sensor. For instance, in a particular embodiment, the induction coil sensor can form a part of a resonant circuit. The output signal can be based at least in part on the resonant frequency of the resonant circuit. In a particular aspect of this exemplary embodiment, the electronic circuit can be adapted to detect the presence of an insult based at least in part on a change in the output signal. The electronic circuit can be configured to determine whether the insult is a urine insult or a feces insult based at least in part on the magnitude of the change in the output signal.

In another particular aspect of this embodiment, the signaling device can further include an electronic nose sensor configured to provide signals associated with the presence of one or more volatile organic compounds in the absorbent article. The electronic circuit can be adapted to determine whether the insult is a urine insult or a feces insult based at least in part on the magnitude of the change in the output signal and the signals received from the electronic nose sensor.

In still another variation of this exemplary embodiment, the sensor can include a capacitive sensor, such as an open face capacitor, adapted to sense a change in capacitance due to an insult in the absorbent article. In a particular embodiment, the sensor can include or be coupled to a resonant circuit. The electronic circuit can be adapted to measure changes in capacitance by measuring changes in the resonant frequency of the resonant circuit. In a particular aspect of this exemplary embodiment, the electronic circuit can be adapted to determine whether the insult is a urine insult or a feces insult based at least in part on monitoring the rate of change in capacitance over time due to an insult in the absorbent article.

In further aspects of this exemplary embodiment, the signaling device can include an attachment mechanism for removably attaching the device to the absorbent article. In another aspect, the signaling device can include a housing, such as a flexible housing. In another aspect, the signaling device can be adapted to provide notification of the presence of an insult in the absorbent article, such as a visual notification, an audio notification, a wireless notification (e.g. communication with a smart phone), vibratory notification, or other suitable notification.

Another exemplary embodiment of the present disclosure is directed to a method for detecting and identifying an insult in an absorbent article. The method includes monitoring an electrical property associated with the absorbent article. The electrical property changes in response to an insult. The method further includes detecting a change in the electrical property to determine the presence of an insult; and analyzing the change in the electrical property to determine whether the insult is a urine insult or a feces insult.

In a variation of this exemplary embodiment, monitoring an electrical property can include monitoring the impedance between a first conductive element and a second conductive element disposed in the absorbent article. The first conductive element and the second conductive element are separated from an absorbent structure in the absorbent article by a barrier layer. In a particular aspect of this exemplary embodiment, detecting a change in an electrical property can include detecting a change in the impedance between the first conductive element and the second conductive element. Analyzing the change in the electrical property can include monitoring the impedance between the first conductive element and the second conductive element for a defined time period after the change in impedance due to an insult; classifying the insult as a urine insult if the impedance returns to within a threshold of its original value within a defined time period after the change in impedance; and classifying the insult as a feces insult if the impedance remains substantially constant within the defined time period after the change in impedance due to the insult.

In another variation of this exemplary embodiment, monitoring an electrical property can include monitoring the impedance of an induction coil sensor located adjacent the absorbent article. In a particular aspect of this exemplary embodiment, detecting a change in the electrical property can include detecting a change in the impedance of the induction coil sensor. Analyzing a change in the electrical property can include determining the magnitude of the change of the impedance of the induction coil and classifying the insult as a urine insult or a feces insult based at least in part on the magnitude of the change in the impedance of the induction coil.

In another particular aspect of this exemplary embodiment, the method can include monitoring the presence of one or more volatile organic compounds due to feces (Gas production by feces of infants, J Pediatric Gastroenterology and Nutrition, 32, 534-541, May 2001) in the absorbent article using an electronic nose sensor. Analyzing a change in the electrical property can include classifying the insult as a urine insult or a feces insult based at least in part on the magnitude of the change in the impedance of the induction coil sensor and the presence of one or more volatile organic compounds in the absorbent article. For instance, the presence of one or more volatile organic compounds can be used to perform a false positive check for false positive signals caused by, for instance, flatus or passing of gases.

In still another variation of this exemplary embodiment, monitoring an electrical property associated with the absorbent article comprises monitoring a capacitance using a capacitive sensor mounted adjacent the absorbent article. In a particular aspect of this exemplary embodiment, detecting a change in the electrical property can include detecting a change in the capacitance. Analyzing the change in the electrical property can include determining the rate of change of capacitance over time and comparing the rate of change to a threshold value to determine whether the insult is a urine insult or a feces insult.

A further exemplary embodiment of the present disclosure is directed to a signaling device system, the system includes an absorbent article having an outer cover with an interior surface and an exterior surface and an absorbent structure positioned adjacent the interior surface of the outer cover. The system further includes a first conductive element and a second conductive element separated from the absorbent structure by a barrier layer preferably located between interior surface and the absorbent structure. The impedance between the first conductive element and the second conductive element changes in response to an insult. The system further includes an electronic circuit configured to be coupled to the first conductive element and the second conductive element. The electronic circuit is configured to detect a change in the impedance between the first conductive element and the second conductive element to determine the presence of an insult. The electronic circuit is further configured to analyze the change in the impedance between the first conductive element and the second conductive element to determine whether the insult is a urine insult or a feces insult.

For instance, in a particular aspect of this exemplary embodiment, the electronic circuit can be configured to classify the insult as a urine insult if the impedance between the first conductive element and the second conductive element returns to within a threshold of its original value within a defined time period after the change in the impedance due to the insult. In another particular aspect, the electronic circuit can be configured to classify the insult as a feces insult if the impedance between the first conductive element and the second conductive element remains substantially constant for a defined time period after the change in the impedance due to the insult.

Still another exemplary embodiment of the present disclosure is directed to a signaling device system for detecting and identifying an insult in an absorbent article. The system includes an induction coil sensor configured to be located adjacent the absorbent article. The induction coil sensor has an impedance that changes in response to an insult. The system further includes an electronic circuit coupled to the induction coil sensor. The electronic circuit is configured to detect a change in the impedance of the induction coil sensor due to an insult. The electronic circuit is further configured to analyze the change in the impedance of the induction coil sensor to determine whether the insult is a urine insult or a feces insult. In a particular aspect of this exemplary embodiment, the electronic circuit can be configured to determine whether the insult is a urine insult or a feces insult based at least in part on the magnitude of the change of the impedance of the induction coil sensor.

In another particular aspect of this exemplary embodiment, the system further includes an electronic nose sensor configured to detect the presence of one or more volatile organic compounds in the absorbent article. The electronic device can be configured to determine whether the insult is a urine insult or a feces insult based at least in part on the magnitude of the change of the impedance of the induction coil sensor and the presence of one or more volatile organic compounds in the absorbent article.

Still a further exemplary embodiment of the present disclosure is directed to a signaling device system that includes a capacitive sensor configured to be located adjacent the absorbent article. The capacitive sensor is configured to detect a change in capacitance due to the presence of an insult. The system further includes an electronic circuit coupled to the capacitive sensor. The electronic circuit is configured to analyze the change in capacitance to determine whether the insult is a urine insult or a feces insult. For instance, in a particular aspect of this exemplary disclosure, the electronic circuit is configured to determine whether the insult is a urine insult or a feces insult based at least in part on the rate of change of capacitance due to the insult.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
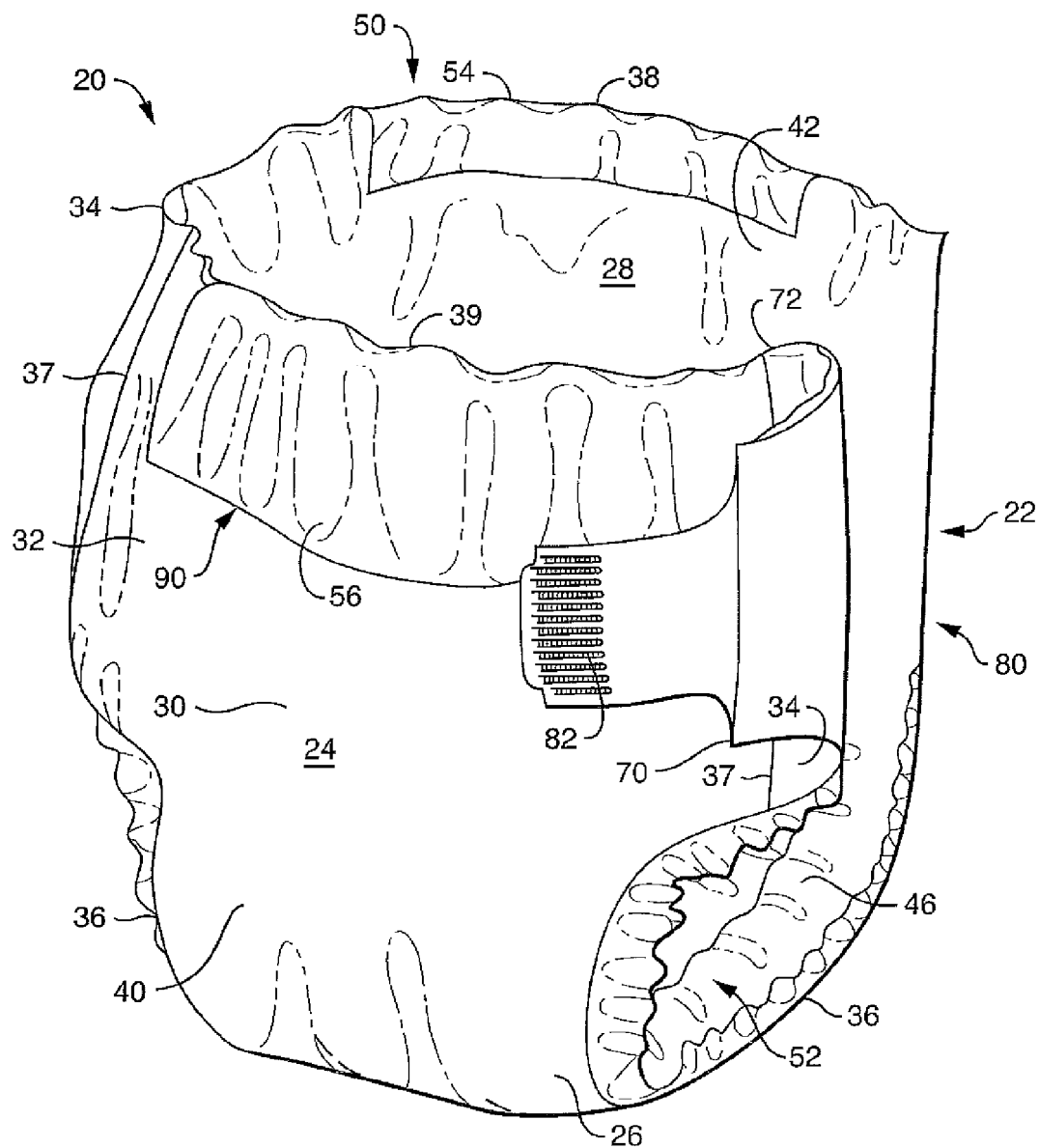
FIG. 1 is a rear perspective view of one embodiment of an absorbent article made in accordance with an exemplary embodiment of the present disclosure.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to a signaling device that can detect the presence of an insult (i.e. body exudates such as urine and/or feces) in an absorbent article or in an undergarment. The signaling device can determine whether the insult is a urine insult or a feces insult. The signaling device can provide a notification to a user that an insult has occurred and can inform the user whether the insult is a urine insult or a feces insult. In this manner, embodiments of the present disclosure provide advantages over wetness signaling systems for absorbent articles known in the art.

Discussion of the exemplary embodiments herein will be made with reference to the absorbent article 20 illustrated in FIGS. 1-4. While the discussion of the exemplary embodiment are made with reference to a diaper, it is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present disclosure. It should also be understood the various exemplary embodiments could also be used to identify and classify an insult in an undergarment if a user would like to monitor the presence of an insult without necessarily requiring an absorbent article.

Figure 2:
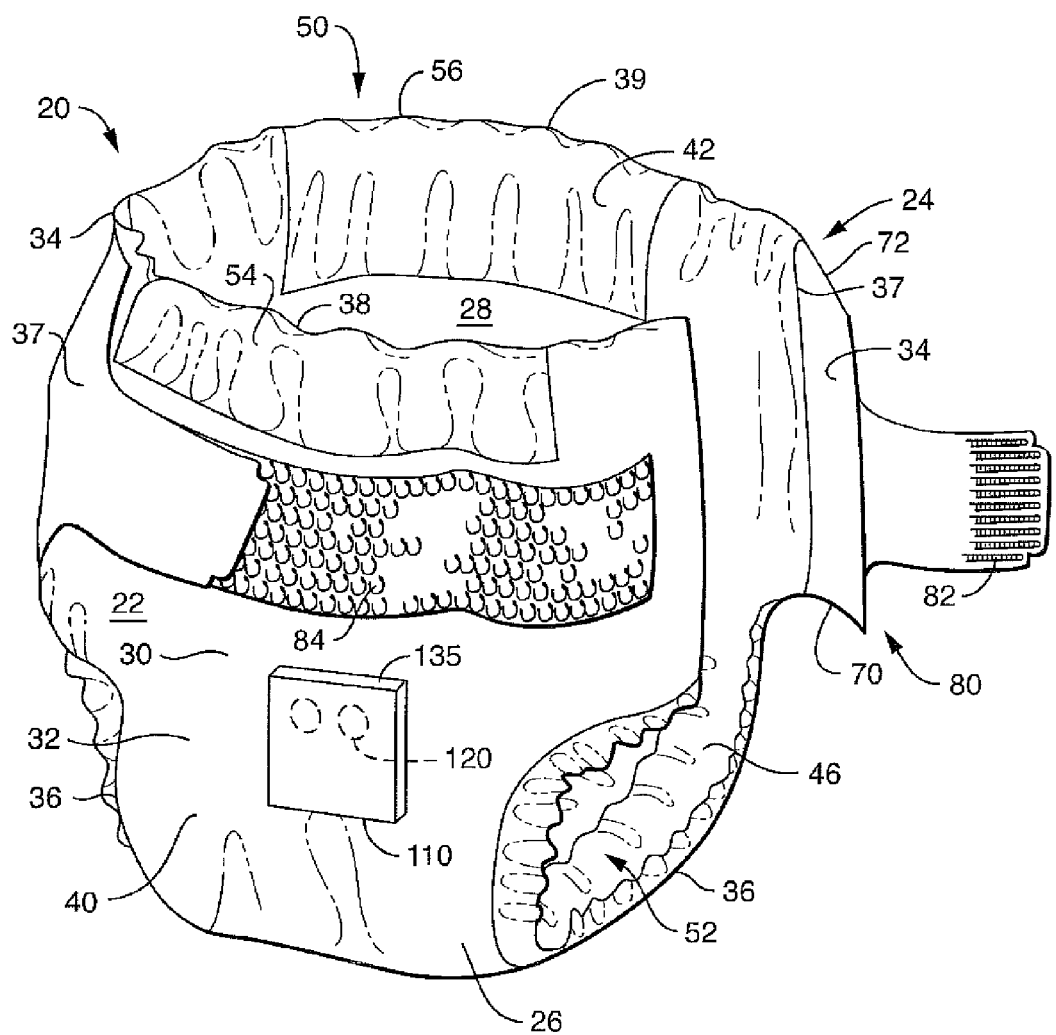
FIG. 2 is a front perspective view of the absorbent article illustrated in FIG. 1 including one aspect of a signaling device according to an exemplary embodiment of the present disclosure.

Referring to FIGS. 1 and 2, for exemplary purposes, an absorbent article 20 that can be used in conjunction with the exemplary signaling systems of the present disclosure is shown. The absorbent article 20 can be disposable or not. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present disclosure.

By way of illustration only, various materials and methods for constructing absorbent articles such as the absorbent article 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel at al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
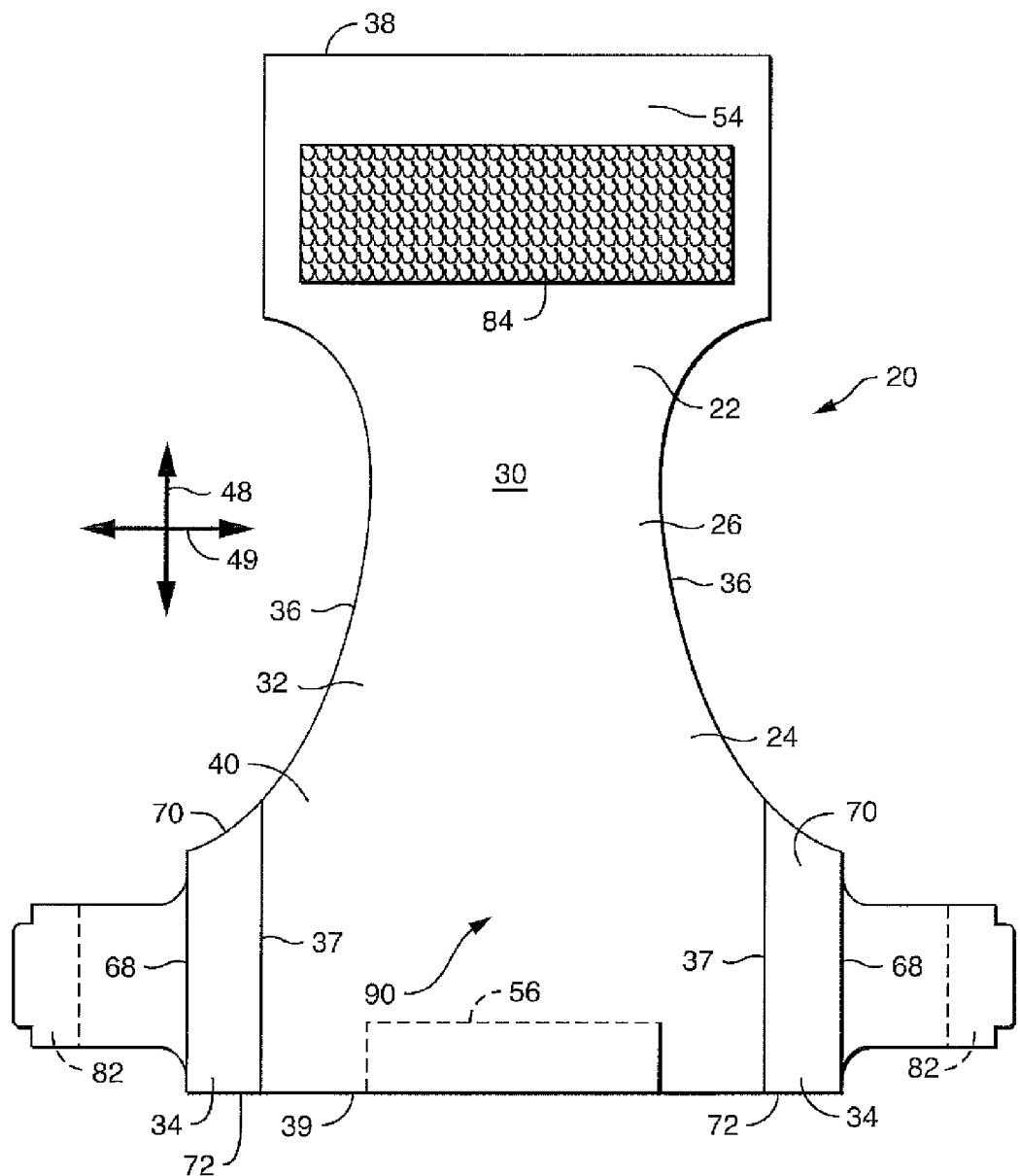
FIG. 3 is a plan view of the absorbent article shown in FIG. 1 with the article in an unfastened, unfolded and laid flat condition showing the surface of the article that faces away from the wearer.
Figure 4:
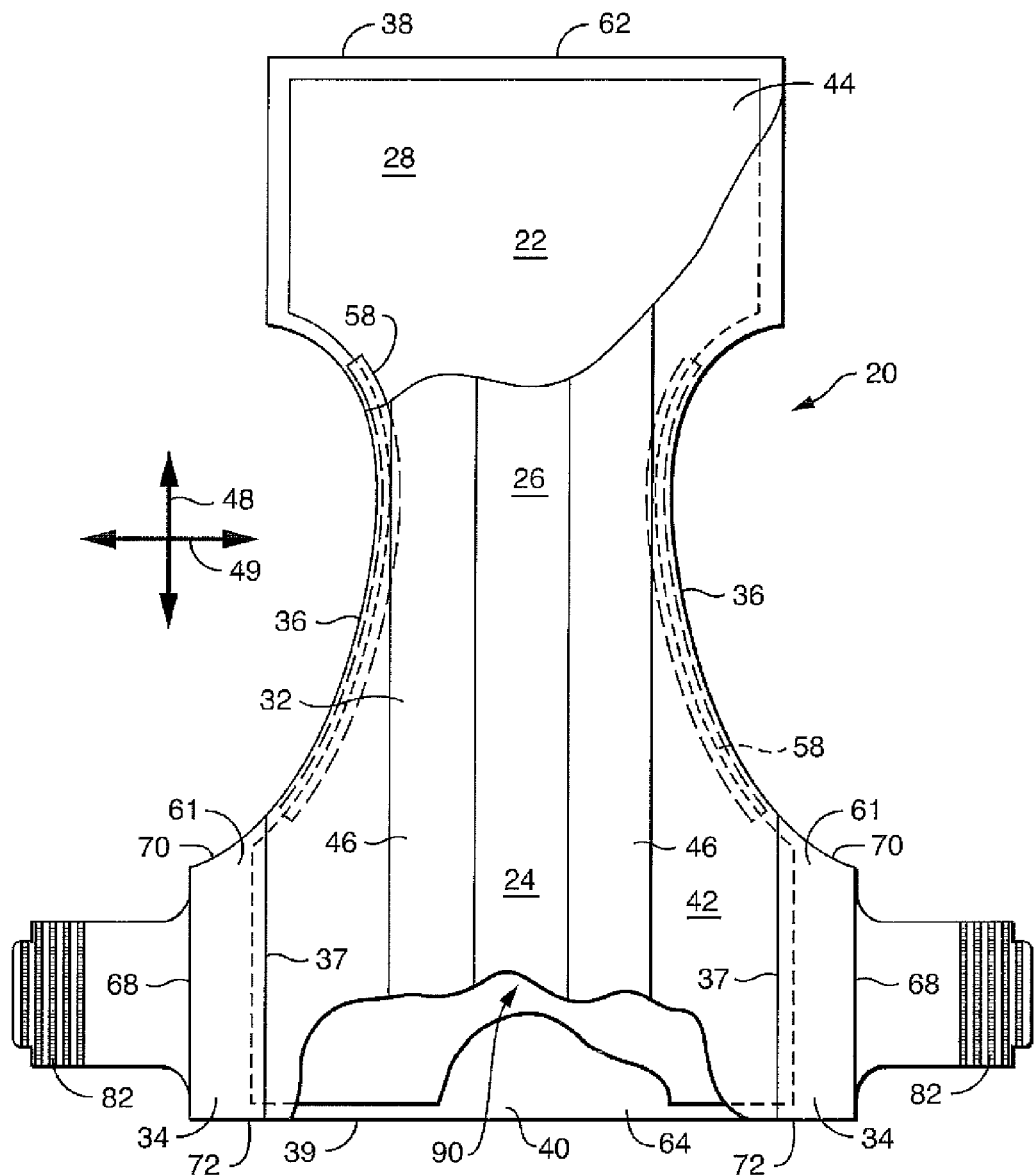
FIG. 4 is a plan view similar to FIG. 3 showing the surface of the absorbent article that faces the wearer when worn and with portions cut away to show underlying features.

An absorbent article 20 is representatively illustrated in FIG. 1 in a partially fastened condition. The absorbent article 20 shown in FIGS. 1 and 2 is also represented in FIGS. 3 and 4 in an opened and unfolded state. Specifically, FIG. 3 is a plan view illustrating the exterior side of the absorbent article 20, while FIG. 4 illustrates the interior side of the absorbent article 20. As shown in FIGS. 3 and 4, the absorbent article 20 defines a longitudinal direction 48 that extends from the front of the article when worn to the back of the article. Orthogonal to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, that, when worn, wholly or partially cover or encircle the waist or mid-lower torso of the wearer. The crotch region 26 generally is that portion of the absorbent article 20 that, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that can be joined to the outer cover 40 in a superimposed relation therewith by adhesives, ultrasonic bonds, thermal bonds or other conventional techniques. Referring to FIG. 4, the liner 42 can suitably be joined to the outer cover 40 along the perimeter of the chassis 32 to form a front waist seam 62 and a back waist seam 64. As shown in FIG. 4, the liner 42 can suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article 20. The chassis 32 can further include an absorbent structure 44 particularly shown in FIG. 4 disposed between the outer cover 40 and the bodyside liner 42 for absorbing liquid body exudates exuded by the wearer, and can further include a pair of containment flaps 46 secured to the bodyside liner 42 for inhibiting the lateral flow of body exudates.

The elasticized containment flaps 46 as shown in FIG. 4 define a partially unattached edge that assumes an upright configuration in at least the crotch region 26 of the absorbent article 20 to form a seal against the wearer's body. The containment flaps 46 can extend longitudinally along the entire length of the chassis 32 or can extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates (e.g. urine and/or feces insults), the absorbent article 20 can also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 can include a plurality of dry-spun coalesced multifilament spandex elastomeric threads sold under the trade name LYCRA and available from Invista, Wilmington, Del., U.S.A.

In some aspects, the absorbent article 20 can further include a surge management layer (not shown) that can be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that can be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 can be stretched around the waist and/or hips of a wearer to secure the garment in place. As shown in FIGS. 3 and 4, the elastic side panels are attached to the chassis along a pair of opposing longitudinal edges 37. The side panels 34 can be attached or bonded to the chassis 32 using any suitable bonding technique. For instance, the side panels 34 can be joined to the chassis by adhesives, ultrasonic bonds, thermal bonds, or other conventional techniques.

In an alternative aspect, the elastic side panels can also be integrally formed with the chassis 32. For instance, the side panels 34 can include an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 can alternatively be connected to the front region of the article 20 and extend over the back region when the article is donned.

With the absorbent article 20 in the fastened position as partially illustrated in FIGS. 1 and 2, the elastic side panels 34 can be connected by a fastening system 80 to define a 3-dimensional absorbent article configuration having a waist opening 50 and a pair of leg openings 52. The waist opening 50 of the article 20 is defined by the waist edges 38 and 39 that encircle the waist of the wearer.

In the aspects shown in the figures, the side panels are releasably attachable to the front region 22 of the article 20 by the fastening system. It should be understood, however, that in other aspects the side panels can be permanently joined to the chassis 32 at each end. The side panels can be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 can be suitably curved and/or angled relative to the lateral direction 49 to provide a better fit around the wearer's legs. However, it is understood that only one of the leg end edges 70 can be curved or angled, such as the leg end edge of the back region 24, or alternatively, neither of the leg end edges can be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 can be slanted or curved as desired. Ultimately, the side panels 34 are generally aligned with a waist region 90 of the chassis.

The fastening system 80 can include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 can be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 can include loop fasteners and the second fastening components 84 can be complementary hook fasteners. In another aspect, the fastening components 82, 84 can be interlocking similar surface fasteners, or adhesive and cohesive fastening elements such as an adhesive fastener and an adhesive-receptive landing zone or material; or the like.

In addition to possibly having elastic side panels, the absorbent article 20 can include various waist elastic members for providing elasticity around the waist opening. For example, as shown in the figures, the absorbent article 20 can include a front waist elastic member 54 and/or a back waist elastic member 56.

Referring to FIG. 2, a signaling device 110 has been located on the absorbent article 20. Signaling device 110 is configured to detect the presence of a substance, such as a urine insult and/or a feces insult, in absorbent article 20 and to provide an audible, visible, wireless, or vibratory signal to the user of absorbent article 20 indicative of the presence of the substance. Signaling device 110 includes a housing 135, sensors 120, and electronic circuitry used to detect the presence of an insult in the absorbent article. Housing 135 can be used to house the various electronic and other components of signaling device 110 and in certain embodiments can be a flexible housing. As discussed in detail below, the electronic circuitry of signaling device 110 is adapted to detect the presence of an insult in the absorbent article 20 and to determine whether the insult is a urine insult or a feces insult. Further details of signaling device 110 can be obtained in, for example, U.S. Patent Application Publication No. 2006/0244614 to Long and entitled "Connection Mechanisms," which is incorporated herein by reference to the extent it is consistent (not in conflict) herewith.

The signaling device 110 can emit an audible and/or a visual signal in order to indicate to the user that the signaling device has detected an insult. The audible signal, for instance, may be as simple as one or more beeps to perhaps emitting a musical tune. In certain exemplary embodiments of the present subject matter, such a musical tune may be gender and age appropriate. Similarly, if the signaling device 110 issues a visible signal, the visible signal may comprise a few lights or an interactive display. In still another embodiment, the signaling device 110 may be configured to vibrate when the circuit within the absorbent article is closed. In some embodiments, the signaling device 110 can use a selected combination or all of the signaling techniques including, but not limited to vibration, visible signals, audio signals, and communication with remote devices, such as a smart phone.

In the aspect of the present disclosure shown in FIG. 2, the signaling device 110 is a single unit that remains attached to or that is adapted to be held in the vicinity of the absorbent article 20. For example, the signaling device may be mounted on the absorbent article 20 and issue a visible signal and/or an audible signal from the article itself.

In various aspects of the present disclosure, the absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the absorbent article 20 may also include other wetness sensing features such as fading ink, appearing ink, a wetness liner, or a cooling component.

Figure 5:
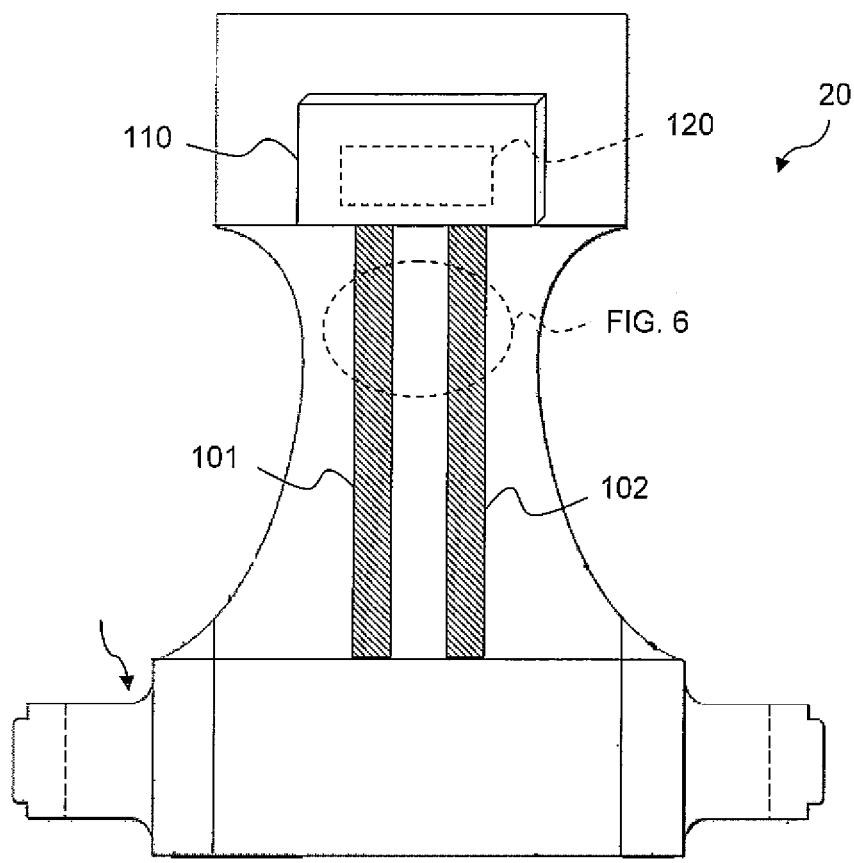
FIG. 5 is a simplified plan view of an absorbent article including an exemplary signaling device system according to a first exemplary embodiment of the present disclosure.

With reference to FIGS. 5-10, a first exemplary signaling system according to an exemplary embodiment of the present disclosure will be discussed in detail. FIG. 5 illustrates a simplified plan view of absorbent article 20 having a first conductive element 101 spaced from a second conductive element 102. In the embodiment illustrated in FIG. 5, the conductive elements 101 and 102 extend through the crotch region of the absorbent article 20 without intersecting. However, the conductive elements 101 and 102 can extend any length of the absorbent article 20 as desired. The conductive elements 101 and 102 can comprise any suitable conductive material, such as a conductive thread, printed conductive lines or a conductive foil. The first conductive element 101 does not intersect the second conductive element 102 in order to form an open circuit that may be closed, for instance, when a conductive fluid or material, such as a urine insult or a feces insult, is positioned between the conductive elements.

Figure 6:
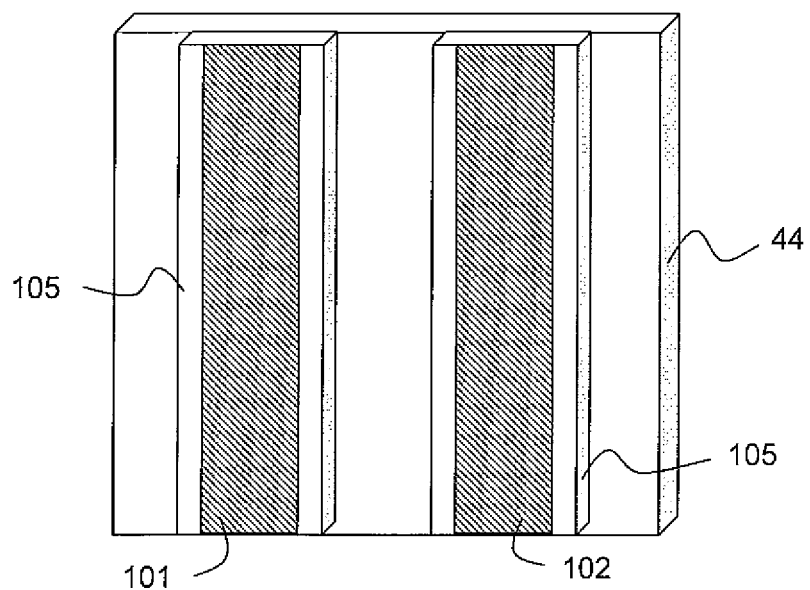
FIG. 6 is a close up view of a first conductive element and a second conductive element disposed on an exemplary absorbent article according to a first exemplary embodiment of the present disclosure.

Conductive elements 101 and 102 may be incorporated into the chassis 32 at any suitable location as long as the conductive elements are positioned so as to contact a body fluid that is exuded by a user. In this regard, the conductive elements 101 and 102 generally lie inside the outer cover 40 of absorbent article 20. As illustrated in FIG. 6, the conductive elements 101 and 102 are separated from the absorbent structure 44 of the absorbent article by a barrier layer 105. Barrier layer 105 may be formed from any suitable material that allows a liquid material, such as urine, to pass through the barrier layer 105 into the absorbent structure 44. Separating the conductive elements 101 and 102 from the absorbent structure 44 using barrier layer 105 permits the detection of multiple insults and permits a signaling device to distinguish between a urine insult and a feces insult.

Referring to FIG. 5, the conductive elements 101 and 102 can be coupled to signaling device 110. Signaling device 110 can be configured to monitor the impedance between the first conductive element 101 and the second conductive element 102. For instance, the signaling device can include a sensor 120 configured to measure the impedance between the first conductive element 101 and the second conductive element 102 and to provide an output signal associated with the impedance. The output signal can be any signal that is generated based at least in part on the impedance between the conductive elements 101 and 102. The signaling device 120 monitors any changes in the impedance due to the presence of an insult in proximity to the conductive elements 101 and 102.

Due to the higher dielectric constant of the insult compared to air, the initial impedance between the conductive elements 101 and 102 drastically changes when an insult is in contact with the conductive elements 101 and 102. When the absorbent article is dry, the conductive elements 101 and 102 exhibit an open or high impedance condition. When the absorbent article has become soiled, the conductive elements 101 and 102, at least temporarily, exhibit a closed or low impedance condition due to the presence of the insult. The sensor 120 can detect the change in impedance due to the insult. The signaling device 110 can provide a notification to a user that an insult has occurred.

The barrier layer 105 permits the signaling device 110 to discriminate between a urine insult and a feces insult. In particular, a liquid or urine insult will pass through the barrier layer 105 to the absorbent structure 44 after a brief period of time. When the urine insult first comes into contact with the conductive elements 101 and 102, the impedance between the conductive elements 101 and 102 drastically decreases due to the conductive path provided by the urine insult. As the urine passes through the barrier layer 105 to the absorbent structure 44, the impedance between the conductive elements 101 and 102 will gradually return to its original value. The signaling device 110 can thus classify an insult as a urine insult if the impedance between the conductive elements 101 and 102 returns to within a threshold of its original value within a defined time period after a change in the impedance due to the occurrence of an insult.

In contrast, a fecal insult will not pass through the barrier layer 105. Rather, a fecal insult will remain between conductive elements 101 and 102. As a result, the impedance between the conductive elements 101 and 102 initially changes upon the occurrence of the fecal insult, but remains substantially constant after the fecal insult. Accordingly, the signaling device 110 can be configured to classify an insult as a fecal insult if the impedance between the conductive elements 101 and 102 remains substantially constant after the occurrence of the insult for a defined time period.

Figure 7:
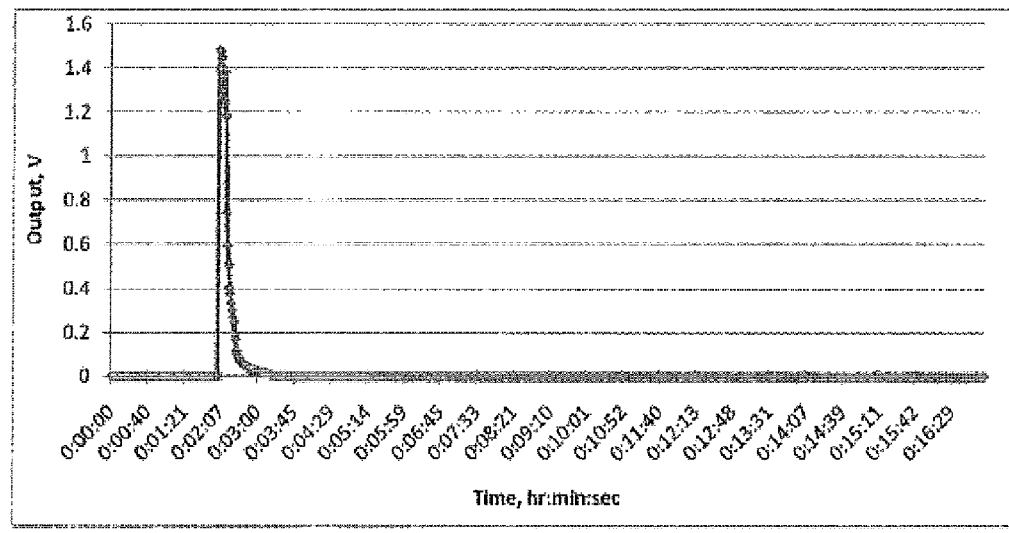
FIG. 7 provides a graphical representation of exemplary sensor output data in response to a urine insult according to a first exemplary embodiment of the present disclosure.
Figure 8:
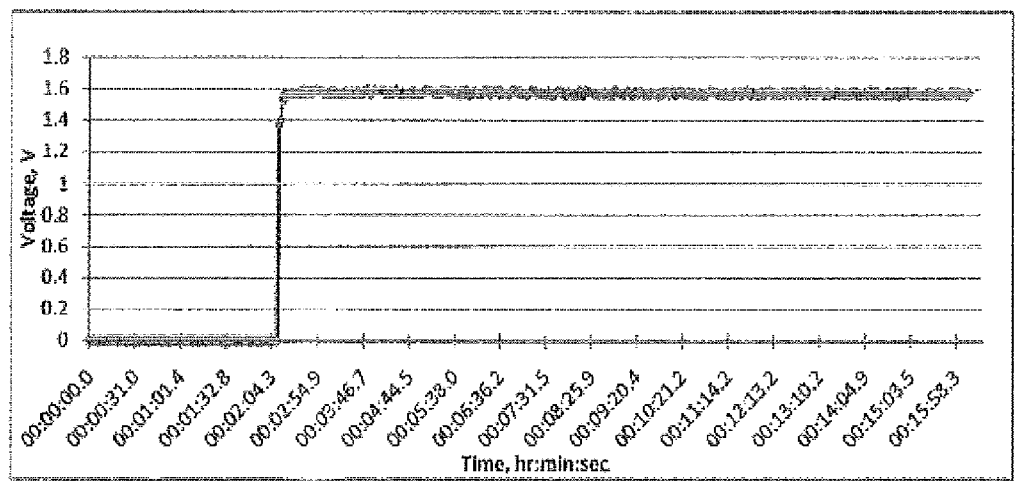
FIG. 8 provides a graphical representation of exemplary sensor output data in response to a feces insult according to a first exemplary embodiment of the present disclosure.

A graphical representation of an exemplary output signal associated with a simulated urine insult and a simulated feces insult is illustrated in FIG. 7 and FIG. 8 respectively. A saline solution with a flow rate of approximately 180 ml/min was used to simulate the urine insult. The output signal illustrated in FIGS. 7 and 8 is associated with the impedance between the first conductive element 101 and the second conductive element 102 such that the voltage of the output signal increases with a decrease in impedance. As illustrated in FIG. 7, the output signal drastically increases in response to a simulated urine insult. However, as the simulated urine insult passes through the barrier layer 105, the output signal returns to within a threshold of its original value after a defined time period.

An output signal associated with simulated feces insult is illustrated in FIG. 8. Felcone (purchased from SiliClone Stuido, Valley Forge, Pa. 19481) was used to simulate the feces insult. As illustrated, the output signal demonstrates a drastic increase in response to the simulated feces insult. However, because the feces insult does not pass through the barrier layer 105, the output signal remains substantially constant after the insult. In this regard, signaling device 120 can discriminate between a urine insult and a feces insult by analyzing the changes in the output signal that occur as a result of the insult.

The barrier layer 105 also permits the detection of multiple insults by the signaling device 120. As discussed above, the barrier layer 105 allows liquid insults, such as a urine insult, to pass through the barrier layer 105 into the absorbent structure 44. As a result, the conductive elements 101 and 102 do not remain in continuous contact with the liquid insult. When the liquid insult passes through the barrier layer 105 to the absorbent structure 44, the impedance between the conductive elements 101 and 102 returns to a value that is within a threshold of its original value. If another insult occurs, the impedance between the conductive elements 101 and 102 will again drastically change, indicating the occurrence of additional insult.

Figure 9:
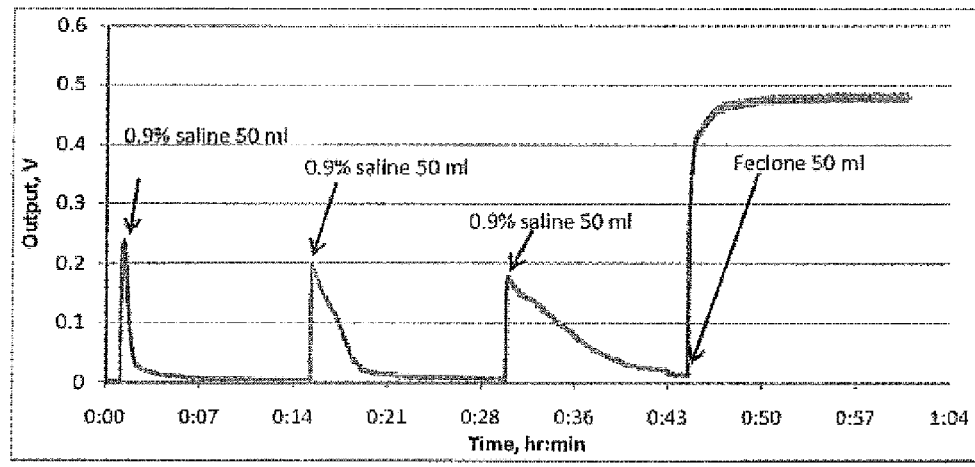
FIG. 9 provides a graphical representation of exemplary sensor output data in response to multiple urine insults and a feces insult according to a first exemplary embodiment of the present disclosure.

FIG. 9 provides a graphical depiction of an output signal associated with multiple insults. The output signal illustrated in FIG. 9 is associated with the impedance between the first conductive element 101 and the second conductive element 102 such that the voltage of the output signal increases with a decrease in impedance. As shown, the output signal initially increases in response to a simulated urine insult. The output signal gradually decreases and returns to within a threshold of its original value as the simulated urine insult passes through the barrier layer 105. Upon the occurrence of an additional simulated urine insult, the output signal again initially increases, indicating the occurrence of the additional insult. This repeats until a simulated feces insult causes the output signal to initially increase and remain substantially constant as a result of the feces insult being unable to pass through the barrier layer 105.

Figure 10:
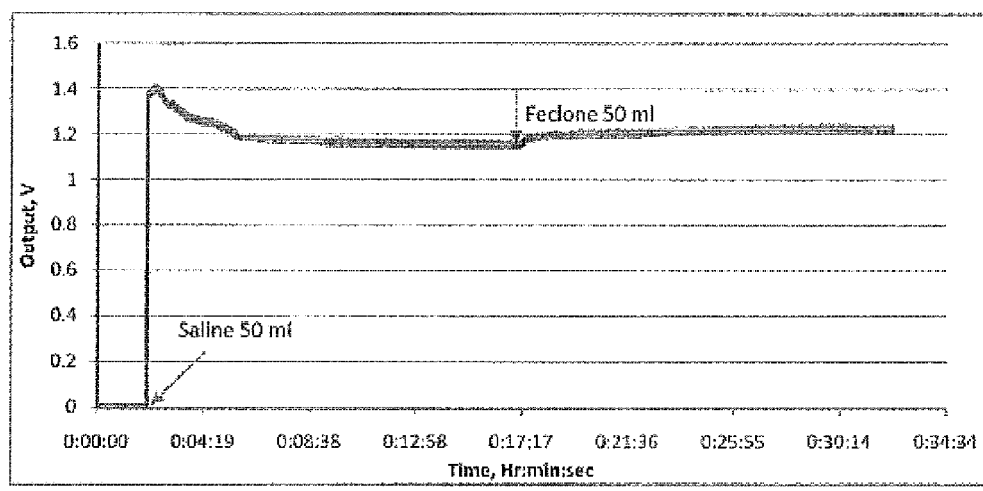
FIG. 10 provides a graphical representation of exemplary sensor output data in response to a urine insult and a feces insult for an absorbent article that includes conductive elements that are not separated from an absorbent structure in the absorbent article by a barrier layer.

FIG. 10 provides a graphical depiction of an output signal associated with multiple insults in an absorbent article that does not include a barrier layer 105 between the conductive elements 101 and 102 and the absorbent structure 44. As illustrated in FIG. 10, the output signal would not indicate the presence of the fecal insult because the output signal did not return to within a threshold of its original value after the simulated urine insult. The simulated urine insult remained in contact with the conductive elements 101 and 102 because there was no barrier layer to shield the conductive elements 101 and 102 from the absorbent structure 44.

Figure 11:
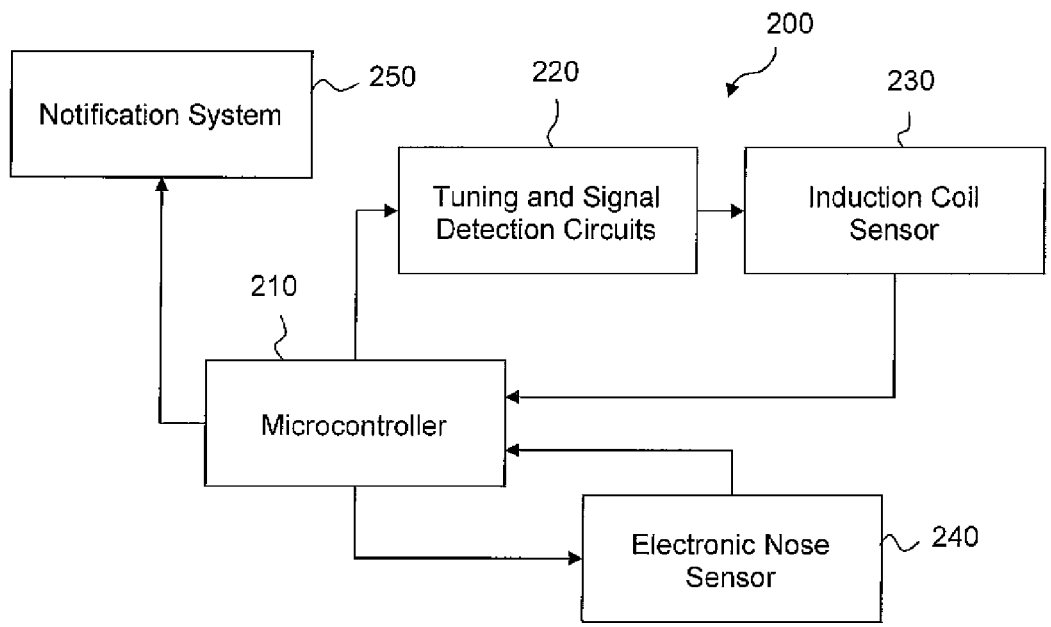
FIG. 11 provides a block diagram of an exemplary signaling system according to a second exemplary embodiment of the present disclosure.
Figure 12:
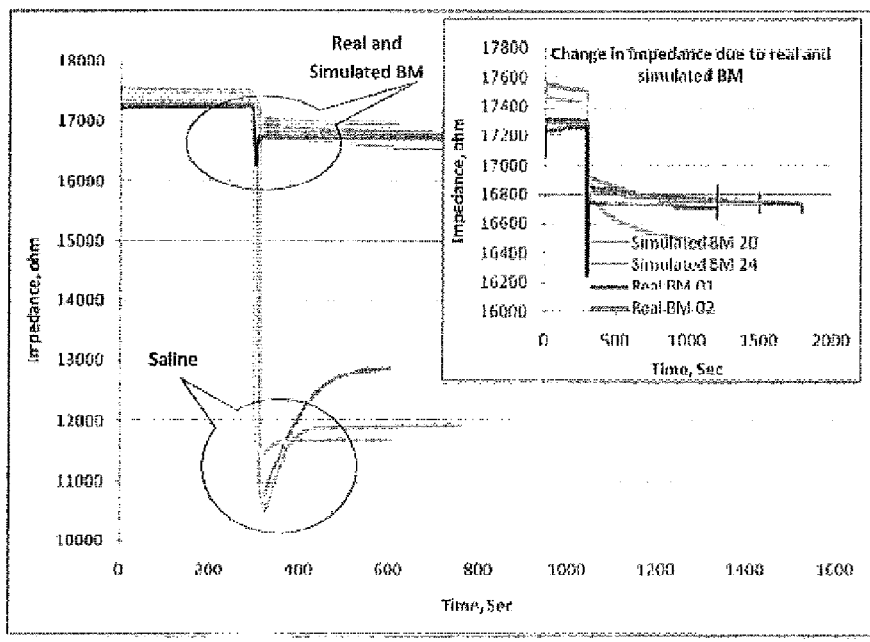
FIG. 12 provides a graphical representation of exemplary sensor output data in response to both urine insults and feces insults according to a second exemplary embodiment of the present disclosure.
Figure 13:
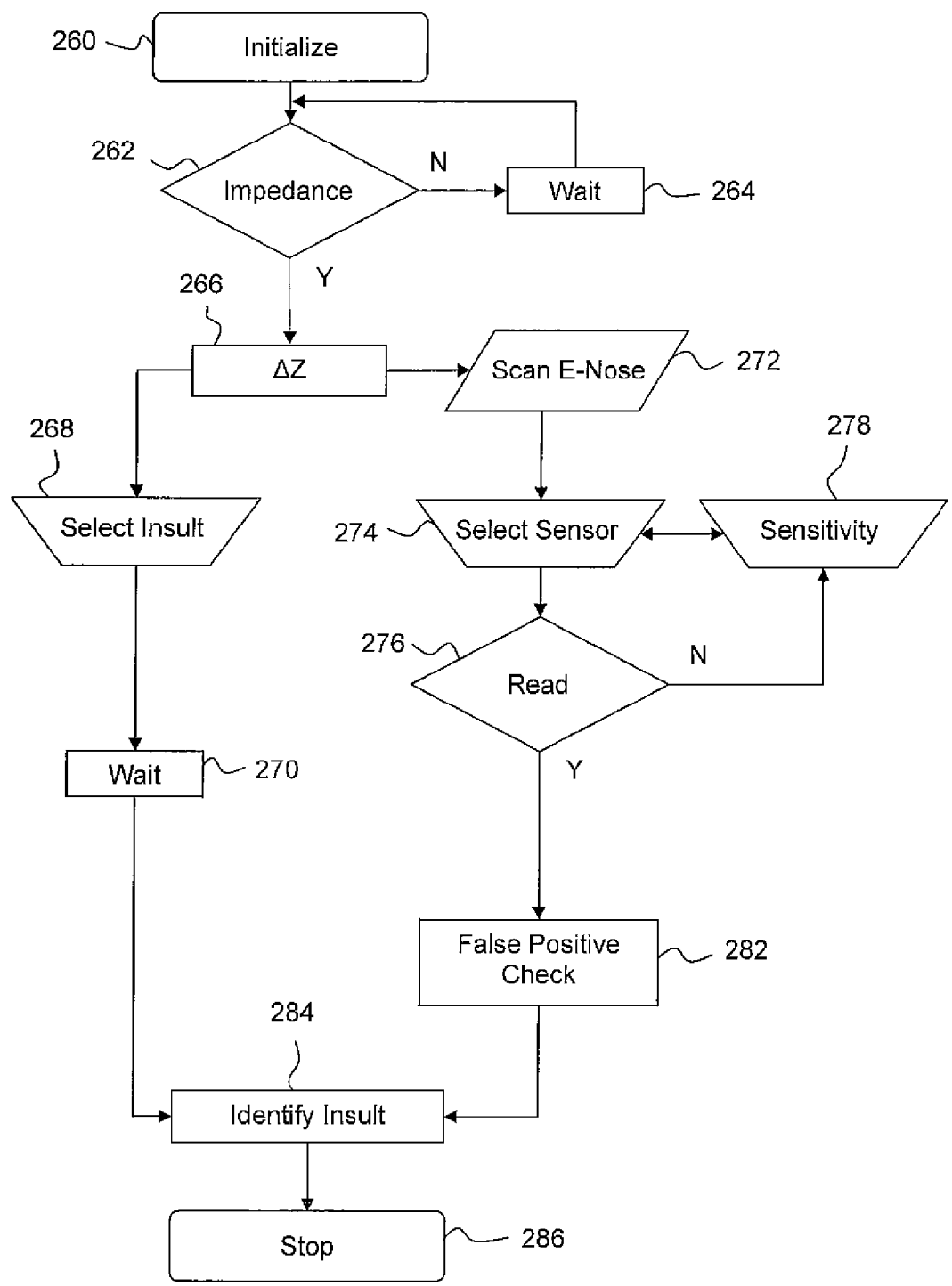
FIG. 13 provides a flow chart of exemplary method steps according to a second exemplary embodiment of the present disclosure.

Referring to FIGS. 11-13 a second exemplary embodiment according to the present disclosure will now be discussed in detail. FIG. 11 illustrates a block diagram of a signaling system 200 that includes a microcontroller 210, tuning and signal detection circuits 220, an induction coil sensor 230, an electronic nose sensor 240, and a notification system 250. When signaling system 200 detects the presence of an insult in an absorbent article, the signaling system 200 provides a notification through notification system 250 to a user. The notification can be a visible, audio, vibratory, wireless and/or other suitable notification.

Signaling system 200 is based on an induction coil sensor 230 and an electronic nose sensor 240. Induction coil sensor 230 is adapted to detect changes in impedance of an induction coil due to the presence of an insult in the absorbent article 20. The electronic nose sensor 240 detects any volatile organic compounds in the absorbent article that may be associated with an insult. Signals from both the induction coil sensor 230 and the electronic nose sensor 240 are used to discriminate between a urine insult and a feces insult.

Details concerning an exemplary induction coil sensor 230 and associated circuitry can be found in U.S. Patent Application Publication No. 2009/0124990 to Feldkamp et al. and entitled "Induction Coil Wetness Sensor for An Absorbent Article" which is incorporated herein by reference to the extent it is consistent (i.e. does not conflict) herewith. The induction coil sensor 230 is adapted to be placed adjacent the absorbent article 20. When excited by a resonant circuit, such as tuning and detection circuit 220, the induction coil sensor 230 generates fields that penetrate into the absorbent article. When the absorbent article become soiled, the induction coil sensor will generate weak electrical eddy currents in the insult. The electrical currents in turn generate a field that couples with the induction coil sensor 230 causing the impedance of the induction coil sensor 230 to change. The microcontroller 210 can detect these changes in impedance to determine the presence of an insult in the absorbent article. The microcontroller 210 can further analyze the changes in the impedance to determine whether the insult is a urine insult or a feces insult.

For instance, in a particular embodiment, the induction coil sensor 230 is coupled to a resonant circuit, such as tuning and detection circuit 220. When the impedance of the induction coil sensor 230 changes as a result of an insult, the resonant frequency of the tuning and detection circuit 220 will also change. The changes in resonant frequency of the tuning and detection circuit 220 can be measured and correlated to an amount of insult.

FIG. 12 provides a graphical representation of an exemplary output signal associated with the impedance of the induction coil sensor 230. Bench tests were conducted using a saline solution to simulate a urine insult, as well as simulated and real fecal insult samples. As illustrated in FIG. 12, the magnitude of change of impedance associated with a urine insult is significantly greater than the magnitude of change of impedance associated with a feces insult.

As a result, the microcontroller 210 can distinguish between a urine insult and a feces insult by analyzing the magnitude of the change in impedance of the induction coil sensor 230. For instance, the microcontroller 210 can determine the magnitude of the change in impedance and compare the magnitude to a threshold value. The microcontroller 210 can classify the insult as a urine insult or a feces insult based on whether the magnitude of the change in impedance is greater or less than the threshold value.

The electronic nose sensor 240 can be implemented using volatile organic gas sensors such as hydrogen sulfide sensors, ammonia sensors, skatole sensors, indole sensors or other suitable sensors. The electronic nose sensor 240 can sense various gases associated with body waste. The gases associated with a urine insult are different from the gases associated with a feces insult. Accordingly, the electronic nose sensor 240 can be used by signaling system 200 to distinguish between a urine insult and a feces insult. For instance, if the impedance change is detected from the inductive sensor 230, the microcontroller 210 can be programmed to look for secondary supporting data from the electronic nose sensor 240. The signals from the electronic nose sensor 240 can be analyzed to distinguish between a urine insult and a feces insult.

FIG. 13 provides a flow chart of an exemplary method executed by microcontroller 210 to distinguish between a urine insult and a feces insult. At 260 the method is initialized. At 262, the microcontroller 210 determines if there has been a change in impedance of the induction coil sensor 230. At 264, if no change has been detected, the microcontroller 210 waits until a change in impedance is detected. At 266, the microcontroller 210 determines the magnitude of the change in impedance of the induction coil sensor 230. At 268, the microcontroller 210 selects a type of insult based on the magnitude of the change in impedance of the induction coil sensor. At 270, the method waits while the microcontroller 210 analyzes signals from the electronic nose sensor 240.

At 272, the microcontroller 210 directs the electronic nose sensor 240 to detect the presence of volatile organic compounds in the absorbent article 20. At 274, a particular electronic nose sensor 240 scans for a particular compound. For instance, an ammonia sensor may scan for an ammonia compound. At 278, the electronic nose sensor 240 determines if the particular compound is present. If the compound is not present, the sensitivity of the sensor 240 can be adjusted as shown at 278 or the electronic nose sensor 240 can scan for a different compound. At 280, after the electronic nose sensor 240 has determined the presence of one or more volatile compounds, the microcontroller 210 can use the presence of the one or more volatile compounds as part of a false positive check.

At 284, the microcontroller 210 classifies the insult as either a urine insult or a feces insult based on the magnitude of the change in impedance of the sensor 230 and based on the data received from the electronic nose sensor 240. At 286, the process is stopped. Once the presence of an insult has been determined and classified, the microcontroller 210 can notify a user through various types of notification through notification system 250.

Referring to FIGS. 14-17, a third exemplary embodiment according to the present disclosure will be discussed in detail. The signaling system 300 includes a plurality of capacitive sensors 310, a microcontroller 322, and a notification system

324. The capacitive sensors 310 are placed adjacent an absorbent article to detect the presence of an insult. The microcontroller 322 analyzes signals from capacitive sensors 310 to detect and identify an insult in an absorbent article. The signaling system 300 can provide an alert to a user through notification system 324 upon the detection and/or identification of an insult. The signaling device includes various supporting circuitry, including a bus 312, a multiplexer 314, a A/D converter 316, a constant current source 318, and a current control circuit 320.

Figure 14:
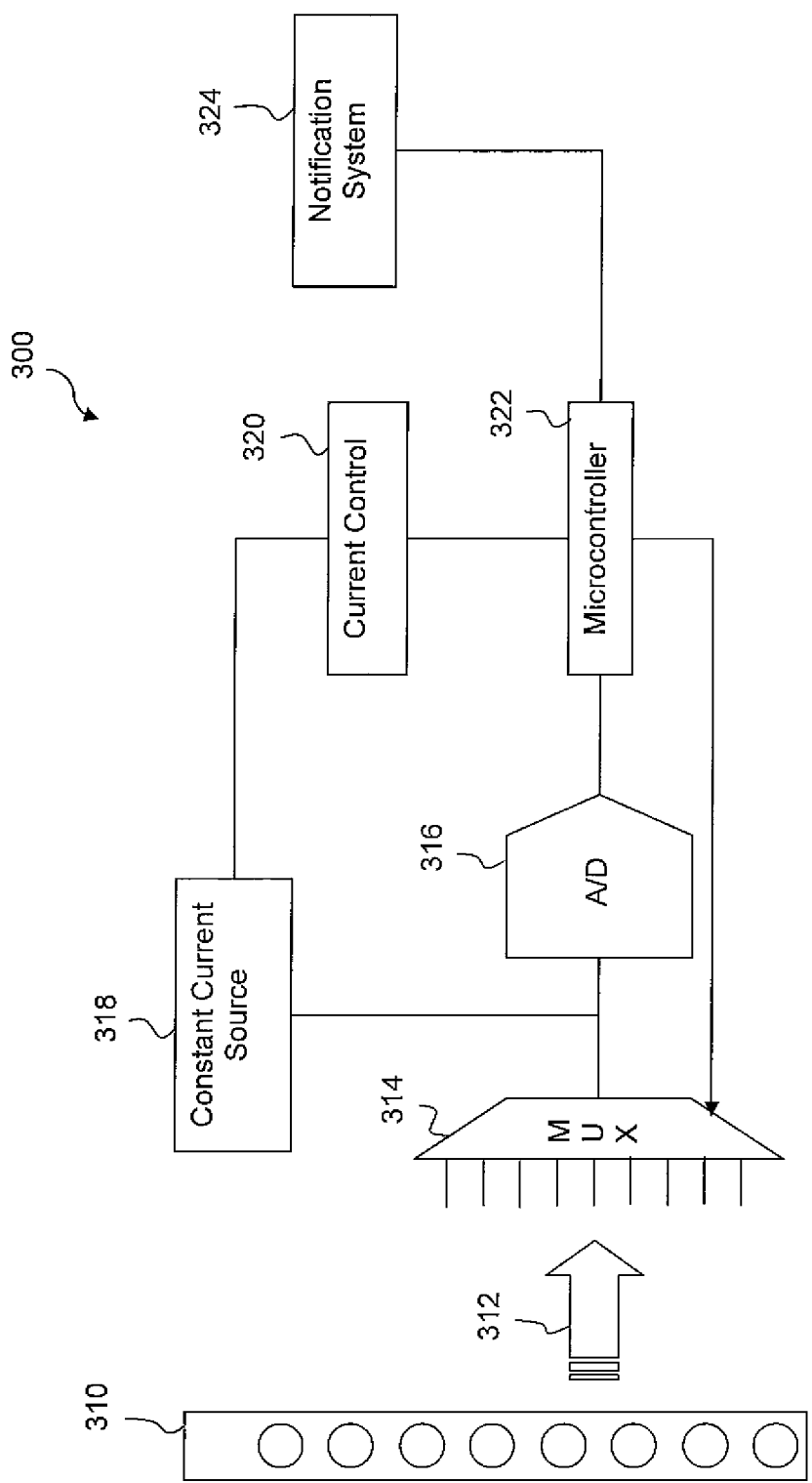
FIG. 14 provides a block diagram of an exemplary signaling system according to a third exemplary embodiment of the present disclosure.

The signaling system of FIG. 14 relies on a plurality of non-invasive capacitive-based sensors 310. Details concerning an exemplary capacitive sensor system and associated circuitry can be found in commonly owned U.S. patent application Ser. No. 12/648,645 which is incorporated herein by reference to the extent it is consistent (i.e. does not conflict) herewith. The capacitive sensors 310 can be used to determine the permittivity of material near the sensing element. The sensing element can take the form of an open face virtual capacitor that, when energized, creates an electrostatic field. For instance, in a particular embodiment, the capacitive sensor 310 can create an electrostatic field that extends beyond the face of the capacitive sensors 310 into the absorbent article 20. Conductive substances such as body exudates in the absorbent article 20 act as dielectrics that change field dynamics, causing a load on the system. The microcontroller 322 can detect these changes in load to determine the presence of an insult in the absorbent article. The microcontroller 322 can further analyze the changes in load to determine whether the insult is a urine insult or a feces insult.

For instance, in a particular embodiment, the capacitive sensors 310 form a part of a resonant circuit. When the capacitance of the capacitive sensors 310 changes as a result of an insult, the resonant frequency of the resonant circuit will also change. The changes in resonant frequency of resonant circuit can be measured and correlated to an amount of insult. In other embodiments, changes in capacitance of the capacitive sensors can be determined, for instance, by measuring the time taken to discharge a capacitor.

The microcontroller 322 can discriminate between a urine insult and a feces insult by analyzing the rate of change or slope of the capacitance of the capacitive sensors 310. The rate of change or slope of the capacitance will be greater for a urine insult than for a feces insult. The absorbent structure 44 of the absorbent article 20 typically absorbs urine insults quickly. This leads to a sharp change in the signal associated with the capacitance for a urine insult. In contrast, a feces insult cannot be absorbed into the absorbent structure 44 of absorbent article 20 quickly. Accordingly the signal associated with the capacitance for a feces insult is typically a slow varying signal. The microcontroller 322 can thus determine whether an insult is a urine insult or a feces insult by determining the slope or rate of change of the capacitance due to the insult.

Figure 15:
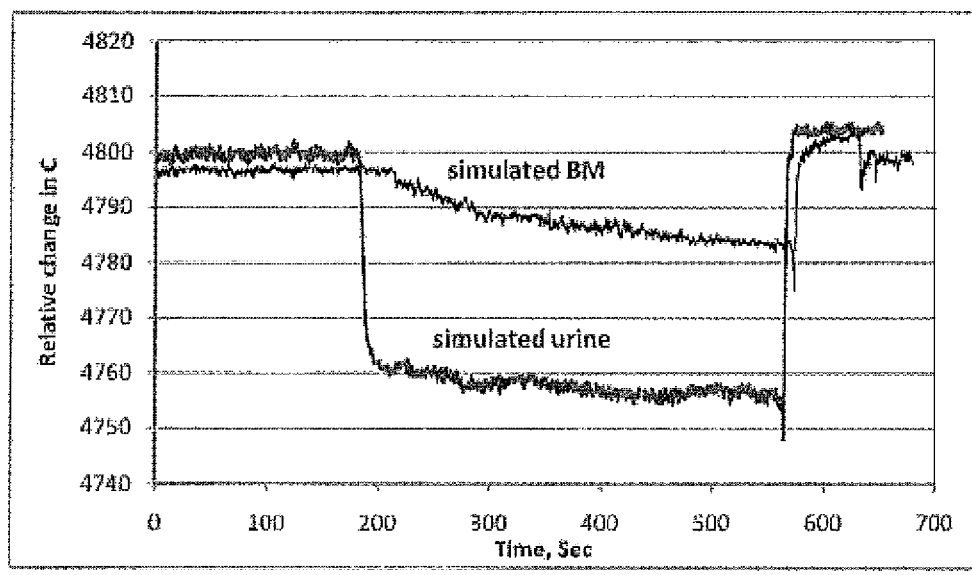
FIG. 15 provides a graphical representation of exemplary sensor output data in response to a urine insult and a feces insult according to a third exemplary embodiment of the present disclosure.
Figure 16:
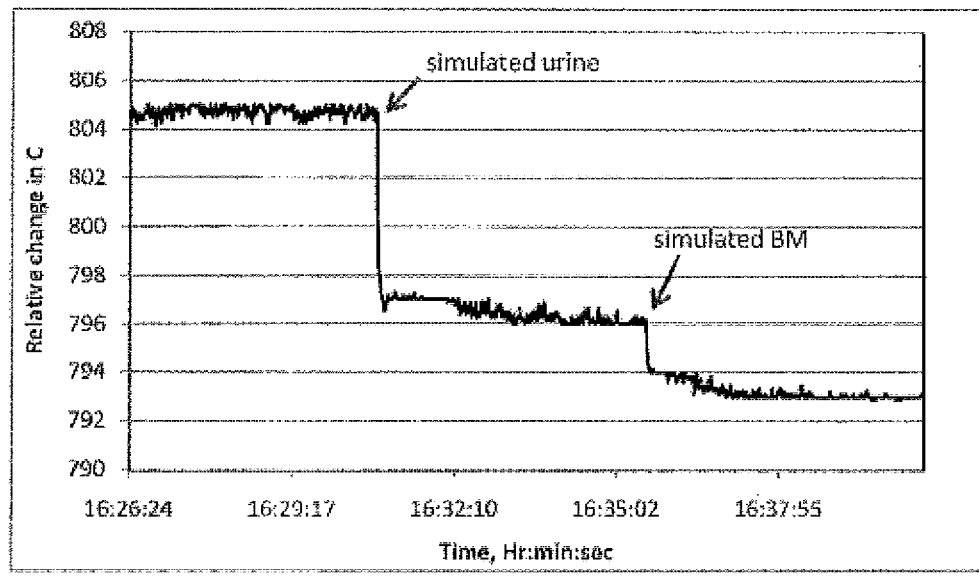
FIG. 16 provides a graphical representation of exemplary sensor output data in response to a urine insult followed by a feces insult according to a third exemplary embodiment of the present disclosure.

For instance, FIGS. 15 and 16 depict exemplary sensor output signals for both urine insults and feces insults. The sensor data depicted in FIGS. 15 and 16 were generated using a saline solution to simulate a urine insult and Felcone to simulate the feces insult. As illustrated, the rate of change of capacitance for a urine insult is significantly greater than the rate of change for a feces insult. In addition, as shown in FIG. 16, a signaling system can detect a feces insult even after the article has been insulted with urine.

The microcontroller 322 can perform a secondary discrimination check based on the location of the particular capacitive sensor that detected the insult. For instance, if the capacitive sensor that detected the insult is located on the front of the absorbent article, the insult is more likely a urine insult. However, if the capacitive sensor is located on the back of the absorbent article, the insult is more likely a feces insult. The second discrimination check can be used to eliminate false positive signals.

Figure 17:
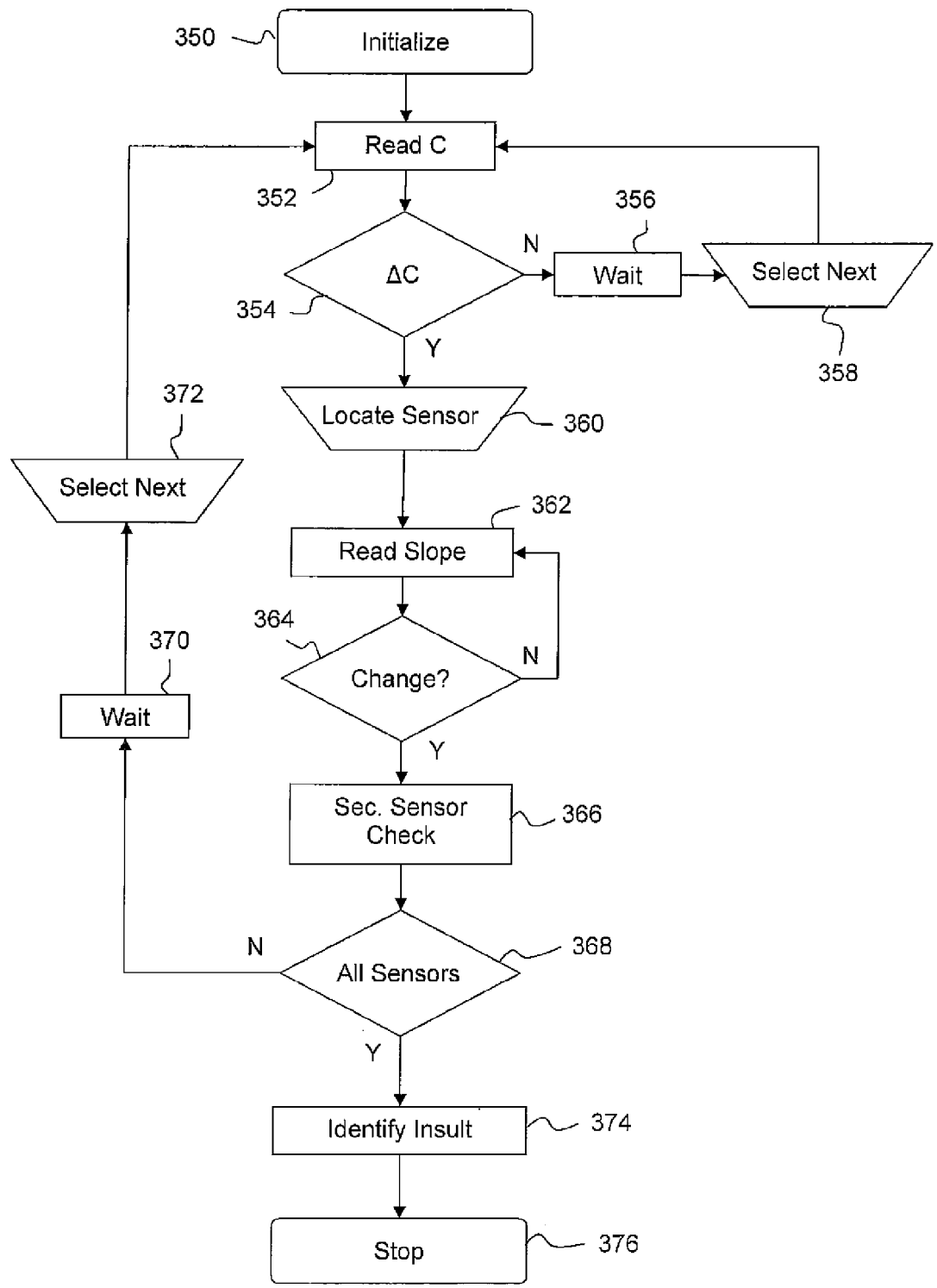
FIG. 17 provides a flow chart of exemplary method steps according to a third exemplary embodiment of the present disclosure.

FIG. 17 provides a flow chart of an exemplary method executed by microcontroller 322 to distinguish between a urine insult and a feces insult. At 350 the method is initialized. At 352, the microcontroller 322 receives capacitance readings from one of the capacitive sensors in the sensor array 310. At 354, the microcontroller 322 determines if there has been a change in capacitance. If no change has been detected, the microcontroller 322 waits at 356 and selects the next capacitive sensor to receive measurements from as shown at 358.

If the microcontroller 322 determines there has been a change in capacitance, the microcontroller 322 determines the location of the capacitive sensor on the absorbent article 20. The microcontroller 322 then reads the slope of the capacitance at 362 and determines whether there has been a change in slope at 364. After the slope readings are performed, the microcontroller 322 can direct a secondary sensor, such as an electronic nose sensor, to perform a check as shown at 366. The microcontroller 322 then determines whether it has received data from all capacitive sensors in the sensor array 310. If the microcontroller 322 has not received signals from all capacitive sensors, the microcontroller 322 waits at 370 and selects the next capacitive sensor as shown at 372. If the microcontroller 322 has received signals from all capacitive sensors, the microcontroller 322 identifies the insult based on the slope of the capacitance, the location of the capacitor, and/or information from one or more secondary sensors as shown at 374. At 376, the process is stopped. Once the presence of an insult has been determined and classified, the microcontroller 322 can notify a user through various types of notification through notification system 324.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A signaling device for detecting and identifying an insult in an absorbent article, the signaling device comprising:
   a sensor configured to provide an output signal associated with an electrical property between a first conductive element and a second conductive element disposed in the absorbent article, wherein the electrical property changes in response to an insult, the first conductive element and the second conductive element positioned in the absorbent article between a body side liner and a barrier layer, the first conductive element and the second conductive element being separated from an absorbent structure in the absorbent article by the barrier layer, and
   an electronic circuit coupled to the sensor, the electronic circuit configured to analyze the output signal to determine whether the insult is a urine insult or a feces insult, the output signal based at least in part on the electrical property between the first conductive element and the second conductive element.

2. The signaling device of claim 1, wherein said sensor comprises an impedance sensor configured to monitor the electrical property, the electrical property comprising an impedance between the first conductive element and the second conductive element disposed in the absorbent article, the first conductive element and the second conductive element being positioned in the absorbent article such that the impedance between the first conductive element and the second conductive element varies in response to an insult in the absorbent article.

3. The signaling device of claim 2, wherein said electronic circuit is configured to classify the insult as a urine insult if the output signal returns to within a threshold of its original value within a defined time period after a change in the output signal due to the insult; said electronic circuit being further configured to classify the insult as a feces insult if the output signal remains substantially constant for a defined time period after a change in the output signal due to the insult.

4. The signaling device of claim 1, wherein said sensor comprises an induction coil sensor located external to the absorbent article, the output signal being based at least in part on the impedance of the induction coil sensor.

5. The signaling device of claim 4, wherein the induction coil sensor comprises a resonant circuit, the output signal being based at least in part on the resonant frequency of the resonant circuit.

6. The signaling device of claim 4, wherein said electronic circuit is adapted to detect the presence of an insult based at least in part on a change in the output signal, said electronic circuit adapted to determine whether the insult is a urine insult or a feces insult based at least in part on the magnitude of the change in the output signal.

7. The signaling device of claim 4, wherein said signaling device further comprises an electronic nose sensor configured to provide signals associated with the presence of one or more volatile organic compounds in the absorbent article, said electronic circuit adapted to determine whether the insult is a urine insult or a feces insult based at least in part on the magnitude of the change in the output signal of the impedance sensor and the signals received from the electronic nose sensor, 8. The signaling device of claim 1, wherein said sensor comprises a capacitive sensor adapted to sense a change in capacitance due to an insult in the absorbent article.

9. The signaling device of claim 8, wherein the capacitive sensor comprises a resonant circuit, said electronic circuit adapted measure changes in capacitance by measuring changes in the resonant frequency of the resonant circuit.

10. The signaling device of claim 8, wherein the electronic circuit is adapted to determine whether the insult is a urine insult or a feces insult based at least in part on monitoring the rate of change in capacitance over time due to an insult in the absorbent article.

11. The signaling device of claim 1, wherein said signaling device comprises a flexible housing and an attachment mechanism for removably attaching the device to the absorbent article.

12. A method for detecting and identifying an insult in an absorbent article, the method comprising:
    monitoring an electrical property between a first conductive element and a second conductive element disposed in the absorbent article the first conductive element and the second conductive element positioned between a body side liner and a barrier layer of the absorbent article, the first conductive element and the second conductive element being separated from an absorbent structure in the absorbent article by the barrier layer, wherein the electrical property changes in response to an insult;
    detecting a change in the electrical property between the first conductive element and the second conductive element to determine the presence of an insult; and
    analyzing the change in the electrical property to determine whether the insult is a urine insult or a feces insult.

13. The method of claim 12, wherein monitoring the electrical property between the first conductive element and the second conductive element disposed in the absorbent article comprises monitoring the impedance between the first conductive element and the second conductive element disposed in the absorbent article.

14. The method of claim 13, wherein detecting the change in an electrical property comprises detecting a change in the impedance between the first conductive element and the second conductive element and wherein analyzing the change in the electrical property comprises:
    monitoring the impedance between the first conductive element and the second conductive element for a defined time period after the change in the impedance due to an insult;
    classifying the insult as a urine insult if the impedance returns to within a threshold of its original value within the defined time period after the change in the impedance; and
    classifying the insult as a feces insult if the impedance remains substantially constant for the defined time period after the change in impedance.

15. The method of claim 12, wherein monitoring the electrical property associated with the absorbent article comprises monitoring the impedance of an induction coil sensor located adjacent the absorbent article.

16. The method of claim 15, wherein detecting the change in the electrical property comprises detecting a change in the impedance of the induction coil sensor and wherein analyzing the change in the electrical property comprises:
    determining the magnitude of the change of the impedance of the induction coil; and
    classifying the insult as a urine insult or a feces insult based at least in part on the magnitude of the change in the impedance of the induction coil.

17. The method of claim 15, wherein the method further comprises monitoring the presence of one or more volatile organic compounds in the absorbent article using an electronic nose sensor.

18. The method of claim 17, wherein detecting a the change in the electrical property comprises detecting a change in the impedance of the induction coil sensor, and wherein analyzing the change in the electrical property comprises:
    determining the magnitude of the change of the impedance of the induction coil; and
    classifying the insult as a urine insult or a feces insult based at least in part on the magnitude of the change in the impedance of the induction coil and based at least in part on the presence of one or more volatile organic compounds in the absorbent article.

19. The method of claim 12, wherein monitoring the electrical property associated with the absorbent article comprises monitoring a capacitance using a capacitive sensor mounted adjacent the absorbent article.

20. The method of claim 12, wherein detecting the change in the electrical property comprises detecting a change in the capacitance, and wherein analyzing the change in the electrical property comprises:
    determining the rate of change of the capacitance over time; and comparing the rate of change to a threshold value to determine whether the insult is a urine insult or a feces insult.

* * * * *